United States Patent [19]
Ligon et al.

[11] Patent Number: 5,266,192
[45] Date of Patent: * Nov. 30, 1993

[54] APPARATUS FOR INTERFACING LIQUID CHROMATOGRAPH WITH MAGNETIC SECTOR SPECTROMETER

[75] Inventors: Woodfin V. Ligon; Steven B. Dorn, both of Schenectady, N.Y.

[73] Assignee: General Electric Company, Schenectady, N.Y.

[*] Notice: The portion of the term of this patent subsequent to Dec. 25, 2007 has been disclaimed.

[21] Appl. No.: 8,867

[22] Filed: Jan. 25, 1993

Related U.S. Application Data

[63] Continuation of Ser. No. 759,285, Sep. 12, 1991, abandoned.

[51] Int. Cl.$^5$ ............................................. B01D 15/08
[52] U.S. Cl. .................................. 210/198.2; 210/656; 250/288
[58] Field of Search .................. 55/15, 17, 257.1, 261, 55/277, 267; 210/656, 748, 149, 177, 180, 182, 198.2; 250/281, 282, 288, 288 A

[56] References Cited

U.S. PATENT DOCUMENTS

| | | | |
|---|---|---|---|
| 3,997,298 | 12/1976 | McLafferty | 250/288 A |
| 4,005,291 | 1/1977 | Arsenault | 250/424 |
| 4,055,987 | 11/1977 | McFadden | 250/288 A |
| 4,112,297 | 9/1978 | Miyagi | 250/288 A |
| 4,160,161 | 7/1979 | Horton | 250/288 A |
| 4,298,795 | 11/1981 | Takeuchi | 250/288 A |
| 4,531,056 | 7/1985 | Labowsky | 250/288 A |
| 4,570,068 | 2/1986 | Sakaira | 250/288 A |
| 4,629,478 | 12/1986 | Browner | 250/288 A |
| 4,647,772 | 3/1987 | Lewis | 250/288 A |
| 4,762,995 | 8/1988 | Browner | 250/288 A |
| 4,814,612 | 3/1989 | Vestal | 250/288 |
| 4,863,491 | 9/1989 | Brandt et al. | 55/15 |
| 4,867,947 | 9/1989 | Andresen | 250/288 A |
| 4,883,958 | 11/1989 | Vestal | 250/288 A |
| 4,891,515 | 1/1990 | Jones | 250/288 A |
| 4,958,529 | 9/1990 | Vestal | 250/288 A |
| 4,960,991 | 10/1990 | Goodley | 250/288 |
| 4,977,785 | 12/1990 | Wiloughby | 250/288 |
| 4,980,057 | 12/1990 | Dorn et al. | 210/198.2 |
| 4,999,493 | 3/1991 | Allen | 250/288 A |
| 5,015,845 | 5/1991 | Allen | 250/288 A |

OTHER PUBLICATIONS

Abstract–The 39th ASMS Conference on Mass Spectrometry and Allied Topics–ThRP2–Chemical Ionization combined with Particle Beam LCMS for magnetic sector mass spectrometers, M. R. Green, et al.–May 19–24, 1991.

Summary–ThRP 2, Chemical Ionization Combined with Particle Beam LCMS for Magnetic Sector Mass Spectrometers–39th Proceedings of the ASMS Conference on Mass Sepectrometry and Allied Topics–May 19–24, 1991, Nashville, Tenn.–pp. 1302–1303.

Primary Examiner—Ernest C. Therkorn
Attorney, Agent, or Firm—William H. Pittman

[57] ABSTRACT

An apparatus and method for combining a liquid chromatograph and a magnetic sector mass spectrometer is described. The liquid chromatograph elution solvent is removed and sample particles relatively free of solvent are transported, without producing an electrical glow discharge, to the magnetic sector mass spectrometer having a chemical ionization source therein.

9 Claims, 6 Drawing Sheets

APPARATUS FOR INTERFACING LIQUID CHROMATOGRAPH WITH MAGNETIC SECTOR SPECTROMETER

This application is a continuation of application Ser. No. 07/759,285, filed Sep. 12, 1991, now abandoned.

FIELD OF THE INVENTION

This invention relates to an improved apparatus and method for interfacing a liquid chromatograph with a magnetic sector mass spectrometer. More particularly, the present invention is directed to the combined facilities of a liquid chromatograph and a high resolution double-focusing magnetic sector mass spectrometer having a chemical ionization source. The method of the present invention includes nebulizing a liquid chromatograph eluate (also known as a liquid chromatograph effluent), separation of a solvent liquid (also known as an eluent), and transport of high boiling substances of interest to the chemical ionization chamber of the magnetic sector mass spectrometer in the form of suspended particles for analysis.

BACKGROUND OF THE INVENTION

Mass spectrometric analysis of gas chromatograph fractions is known. It has been recognized that certain classes of organic substances while amenable to mass spectrometric analysis cannot be separated by passing through a gas chromatograph. Therefore, some other means of separating such materials is required as preparation for mass spectrum studies and identification.

A common method for separating aforementioned materials is through liquid chromatography. Liquid chromatography is typically used in analyzing substances comprising large or polar molecules that are unsuitable for gas chromatography.

Liquid chromatography provides a means for separating complex mixtures of either organic or inorganic mixtures into their various components, for example, compounds that are thermally unstable or nonvolatile under normal gas chromatographic conditions.

Another widely used technique for determining structures of chemical species is mass spectrometry. Mass spectrometry identifies an unknown species by comparing its mass spectrum with a reference mass spectrum obtained from a species of known composition. Mass spectrometers generally employ electron impact ionization source for generating ions from the sample material supplied to it.

In liquid chromatography, a chromatographic solvent containing a mixture of components in solution, is passed through a chromatographic column. The chromatographic column separates the mixture, by differential retention in a stationary phase of the column, into its various components. The components emerge from the column as distinct bands in a solvent stream separated in time and therefore distinguishable by the relative retention times. Thus, a liquid chromatograph provides means for sequentially separating individual components from an initially complex mixture which then may be introduced into a detection device, such as a mass spectrometer.

Even though, liquid chromatography provides means for separating a complex mixture into its components, some interfacing means must be provided to remove the liquid chromatograph eluent from these components before their introduction into a detection device, such as a magnetic sector mass spectrometer. Without the removal of the eluent from the component of the mixture before its entry into the ionization chamber of the magnetic sector mass spectrometer, the mass spectra obtained therefrom cannot be used for precise identification of the compounds present in the component.

The organic liquids used as eluents in liquid chromatograph, if present even in minute amounts, constitute a major source of error in any subsequent mass spectrometric analysis. Such an error occurs because the eluate exiting from the liquid chromatographic column generally contains the component in the range of about 10–100 parts per million (ppm). If one were to directly introduce the eluate containing the component into the ionization chamber of the magnetic sector mass spectrometer, the detection system of the magnetic sector mass spectrometer will be overwhelmed by the eluent and detection of the component may not occur. Additionally, the vacuum system of the magnetic sector mass spectrometer will be inundated by the eluent. As a result, an interfacing means and method which removes the eluent while efficiently transferring the material of interest to the magnetic sector mass spectrometer is needed and is provided by this invention.

However, conventional mass spectrometers having the electron impact mode of ionization have limited applications. One of the shortcomings of conventional electron impact mass spectrometry is that many types of compounds give a very weak signal for the molecular ion being analyzed, even when the molecular ion has as high as 1 or 2% relative abundance. This often means that a significantly higher quantity of the sample is required for determining its molecular weight. As a result, chemical ionization mass spectrometry has recently emerged as an important new technique to obtain additional information not provided by electron impact methods.

The extensive molecular fragmentation observed in the electron impact spectra of many compounds results from the fact that during the initial electron/molecule interaction, many molecules receive considerable energy above the ionization voltage. Typically, the molecule ion undergoes one or more bond breaks thereby reducing the intensity of the parent ion. As a result it is difficult to determine with certainty the molecular weight of the parent ion on the basis of the electron impact spectra.

When compared, a chemical ionization mass spectrum obtained from an unfragmented parent molecule provides fairly precise information about the molecular weight of the parent molecule being analyzed. In addition, the chemical ionization fragmentation patterns may differ sufficiently from the electron impact patterns to reveal other structural features not indicated by the conventional mass spectrum.

One of the major problems encountered in connecting liquid chromatograph/mass spectrometer (LC/MS) interfaces to magnetic sector mass spectrometers having chemical ionization sources is the presence of a very high voltage associated with the ion acceleration process. The high voltage between the chemical ionization source and a conventional LC/MS interface can result in an electrical glow discharge. This glow discharge produces a conductive path, which is very damaging to the highly sensitive equipments used in mass spectrometry.

Dorn et al. in U.S. Pat. No. 4,980,057 disclose the use of a nebulizer having a combination ultrasonic/- pneumatic nebulizing means, the use of a heater directly in the gas stream of the evaporation chamber and the control of this heater using a thermocouple located near the inlet of the nozzle, the use of a momentum separator in which the skimmers are symmetrically pumped from two directions in order to minimize turbulence and the use of a three-stage momentum separator which produces significantly low pressures at the magnetic sector mass spectrometer while maintaining a high yield of sample particles. The use of an ultrasonic nebulizer gives much greater flexibility compared to other designs because there is no need to readjust the nebulizer temperature when solvents change (gradient elution techniques) as with prior art thermospray nebulizers. Further, using an ultrasonic nebulizer, the inert gas flow may be adjusted at will to accommodate changing liquid chromatograph flow rates and solvent volatility. However, no apparatus or method for connecting a liquid chromatograph to a magnetic sector mass spectrometer having a chemical ionization source therein is disclosed.

Another interface device utilizing particle beam technology is currently marketed by Hewlett-Packard Company. This device, disclosed in U.S. Pat. No. 4,863,491 to Brandt et al., uses a pneumatic nebulizer and a two stage momentum separator, The stated sensitivity specification for the Hewlett-Packard device is a signal/noise ratio of 50:1 on the molecular ion of caffeine using a sample size of $20 \times 10^{-9}$ g and an LC flow of 0.5 ml/min. methanol.

STATEMENT OF THE INVENTION

The present invention is directed to an apparatus for interfacing a liquid chromatograph with a magnetic sector mass spectrometer having a chemical ionization source therein, the apparatus comprising, nebulizing means for nebulizing under partial vacuum a chromatograph effluent and dispersing the resultant particles by a flow of inert gas to produce an aerosol stream of the particles, evaporation means for evaporating liquid chromatograph solvent from the stream, the evaporation means having heater means therein for maintaining the temperature of the aerosol stream of particles and for compensating the cooling of the stream of the effluent due to evaporation of the liquid chromatograph solvent, a momentum separator connected to the evaporation means, the momentum separator having means for providing momentum to sample particles in the stream and further having vacuum means for removing the gaseous components present in the stream, and restricting means connected to the momentum separator and to a chemical ionization block of the chemical ionization source, the restricting means having a single opening small enough to restrict the outward flow of a reactant gas from the block to the momentum separator but large enough to transport the sample particles from the momentum separator to the chemical ionization block of the chemical ionization source.

Other advantages of the invention will become apparent upon reading the following detailed description and appended claims, and upon reference to the accompanying drawings.

BRIEF DESCRIPTION OF THE DRAWINGS

For a more complete understanding of this invention reference should now be had to the embodiments illustrated in greater detail in the accompanying drawings and described below by way of examples of the invention.

DETAILED DESCRIPTION OF THE PREFERRED EMBODIMENT

This invention contemplates providing a substantially solvent-free sample of a high boiling organic or inorganic chemical species or compound in a finely divided particulate form for delivery into the chemical ionization source of a magnetic sector mass spectrometer. The invention includes an apparatus for interfacing a liquid chromatograph with a high resolution double focusing magnetic sector mass spectrometer having a chemical ionization source therein.

Figure 1:
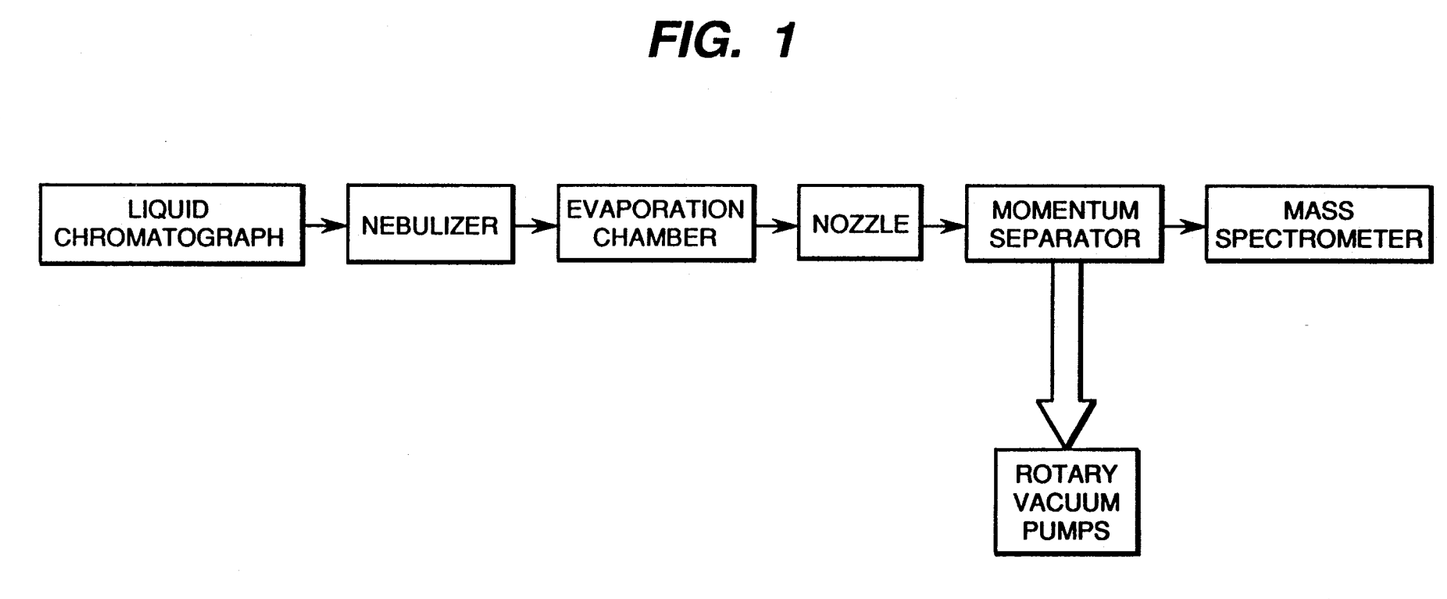
FIG. 1 is a block diagram of the apparatus of the present invention.

FIG. 1 shows a block diagram generally indicating the path of travel of the material being analyzed in the apparatus of the present invention. The material to be tested is initially isolated in the liquid chromatograph. The sample solute-containing liquid chromatograph elution solvent then passes to nebulizing means, such as an ultrasonic nebulizer for nebulizing the liquid chromatograph effluent. The nebulizing means forms an aerosol comprising the liquid chromatograph solution of the high boiling material in the form of small suspended droplets. After formation in the nebulizing means, the aerosol is conveyed to evaporation means by an inert carrier gas, such as helium introduced in the nebulizing means. The eluent contained in the aerosol is vaporized upon its passage through the evaporation means so that the sample material in the form of solid particles is carried by the stream of the inert carrier gas to the magnetic sector mass spectrometer. Evaporation of the solvent may cause cooling of the aerosol sufficient to result in reduced evaporation. Heat, as needed, is provided by heating the mixture of the aerosol and the inert carrier gas. The heat necessary for vaporization of the solvent can be provided by a feedback controlled heater within the evaporation chamber. As the particles reach the end of the evaporation chamber, the solid particles are almost completely solvent-free when at the entrance to the nozzle of the momentum separator. The pumping action of the momentum separator causes the solid particles to accelerate to sonic velocities. After the aforementioned acceleration, the solvent vapor and carrier gas are extracted from the stream by vacuum pumps as described more fully below. The solvent-free sample then travels as a bead of particles through restricting means into the chemical ionization source of the magnetic sector mass spectrometer for analysis. The restricting means are adopted to prevent a glow discharge between the chemical ionization source and the components of the interface.

The liquid chromatograph may be of any conventional design such as a Waters model 600 MS, supplied by Waters Inc., Milford, Mass. and the chromatograph may also include a UV detector such as Waters model 484 MS UV detector connected in series just before the nebulizer of the interface apparatus. In the preferred embodiment, it is essential that the UV detector be capable of operating under sustained back pressures of several thousand psi without damage.

The magnetic sector mass spectrometer may be of any conventional design such as model JEOL SX102, supplied by JEOL USA, Peabody, Mass.

Figure 2:
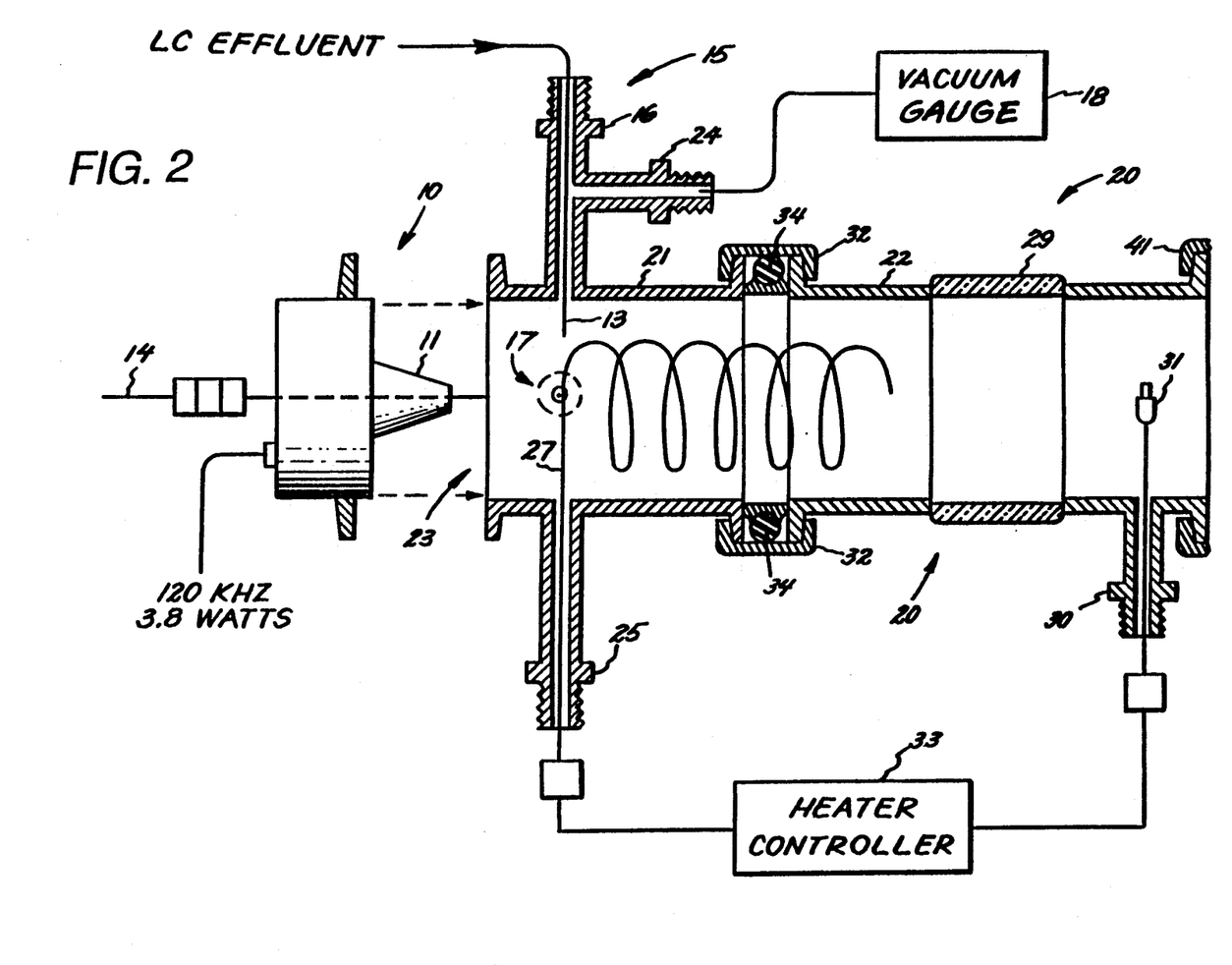
FIG. 2 is a detailed drawing of the nebulizer and evaporation chamber.

FIG. 2 shows a nebulizing means or a nebulizer 10 and evaporation means or evaporation chamber 20. Evaporation means 20 preferably comprises a first section 21 and a second section 22, each preferably being about 1.4 in. inner diameter tube fitted at each end with flanges. Nebulizer 10 is mounted at end 23 of first section 21 of evaporation means 20 and first section 21 is further provided with compression type fittings 16, 24 and 25. For the sake of clarity, FIG. 2 shows nebulizer 10 separated from end 23 of first section 21. Fitting 24 serves as the connection to a vacuum gauge 18 used for monitoring pressure inside evaporation means 20. Nebulizing means 10 may be mounted for stability on support means, such as on a conventional KF-40 flange (not shown). Nebulizing means 10 can be a standard commercial unit obtained from Sonotek Corporation, Poughkeepsie, N.Y., such as their model 8700, modified to provide the improved results of the present invention.

It has been found that because the nebulizer must operate in a partial vacuum, a conventional method of introducing liquid effluent directly from the liquid chromatograph into the nebulizer may produce extensive "bumping" of solvent which may result in serious disruption of the nebulizer operation. "Bumping" is defined as a violent intermittent vaporization of the liquid chromatograph effluent. In order to avoid this problem, a very narrow capillary tube is employed to deliver the the liquid chromatograph effluent or eluent. The capillary maintains a high pressure and prevents bumping. Due to a constriction created by the narrow inner diameter of the inlet line, large back pressures are produced at the outlet end of the liquid chromatograph. Thus by keeping the liquid chromatograph effluent under high pressure until it reaches the tip of horn 11, the "bumping" phenomenon, experienced previously, is nearly eliminated.

This is accomplished by means of a supply tube which is directed substantially perpendicular or at an acute angle with respect to the flow of inert gas. In a typical commercial unit, such as the one mentioned above, the liquid effluent is supplied axially to the tip of horn 11, via a compression fitting at the rear of the unit. Tube assembly 15 preferably comprises a stainless steel outer portion having about 1.6 mm outer diameter and about 0.230 mm inner diameter and an inner portion comprising capillary tube 13, preferably of fused silica having an inner diameter of about 0.1 mm. The outer portion serves to support and align fused silica tube 13. The stainless steel outer portion preferably extends to within about 2 mm of the tip of nebulizer horn 11, while fused silica tube 13 extends beyond the stainless steel outer portion preferably to within about 0.5 mm of the tip of nebulizer horn 11 when nebulizer 10 is inserted in place in first section 21 of evaporation chamber 20. Fused silica tube 13 is connected to an output end of the liquid chromatograph for transporting the liquid chromatograph effluent into evaporation means 20. In nebulizing means 10 of the present invention, the liquid chromatograph effluent is delivered obliquely or orthogonally to a tip of an ultrasonic horn 11 rather than axially as is the case in commercial nebulizers.

Prior art nebulization methods are either pneumatic or thermal (i.e. thermospray). In the present invention, the nebulizing means is a hybrid which is both ultrasonic and pneumatic. Accordingly, the nebulizing means is far less solvent dependent than the prior art nebulizers.

The invention may also include means for adding a second solvent stream directly at the tip of horn 11 by means of a second tube assembly 17 and compression fittings similar to those of tube assembly 15. To those skilled in the art, it would be obvious to provide more than two tube assemblies for delivering chromatograph effluents from several liquid chromatographs. The nebulizers used in the prior art generally need to combine solvent streams before reaching the nebulizer. As a result, there exists the possibility of solvent/solute incompatibility that can result in a precipitation of solute. Such a precipitation can clog the lines. The present invention solves this problem by mixing on the surface of nebulizer 10. The mixing of a second flow of solvent also may be used to reduce peak broadening by providing a rinsing function of the nebulizer surface without loss of sensitivity.

Addition of the second solvent stream near nebulizing means 10 itself, instead of at some earlier point, ensures that the added solvent or solvent plus additive would not have detrimental effects on the UV detector response and would not cause precipitation of solute in the detector or in the interconnecting lines.

In order to disperse an aerosol produced by nebulizer 10, the original liquid supply connection of nebulizer 10 is used to supply a jet of an inert gas, such as helium, from a tank to the tip of horn 11. This may be accomplished by providing a tube 14, preferably of fused silica having about 0.32 mm inner diameter, inside nebulizer's original axial supply orifice at a point approximately 1 cm back from the tip of horn 11. Fused silica tube 14 is preferably held in a well centered position within the original axial supply tubing by a compression union. The inside diameter of the central portion of the union is reduced for inserting fused silica tube 14 therein. Fused silica tube 14 provides enough restriction to give a high gas velocity at the desired flow rates of the inert gas. The preferred inert gas flow rate is about 1 liter/min. However, rates ranging from 300 ml to several liters per minute can be used.

A coiled heater within the evaporation means is considerably more effective and permits more accurate temperature control through the use of a feedback temperature controller than conventional evaporation means used in the prior art. A heater 27, preferably a coiled heater such as a 3 foot long by 1/16 in. calrod type stainless steel heater, enters through fitting 25 and is then positioned in the free space inside first and second sections 21 and 22 respectively.

Second section 22 of evaporation means 20 may be fitted with a sealed glass section 29 near its center to allow a visual evaluation of the relative dryness of the aerosol being produced within evaporation means 20. In addition, this part of evaporation means 20 is preferably fitted with a suitable compression fitting 30 for mounting of a thermocouple probe 31, preferably just in front of an entrance to a nozzle of the momentum separator shown in FIG. 3. The thermocouple is used to sense the temperature of the gas just before the nozzle of the momentum separator. The temperature of the gas at that point is used to control the current applied to heater 27. The output of thermocouple 31 is monitored by a temperature controller 33 to modulate the current supplied to heater 27 mounted in evaporation means 20. The temperature of the inert gas/solvent vapor mix is usually set at a temperature of about 80° to 90° F. by using temperature controller 33. First and second sections 21 and 22 respectively are joined by flange means 32, O-rings 34 and centering rings (not shown).

Figure 3:
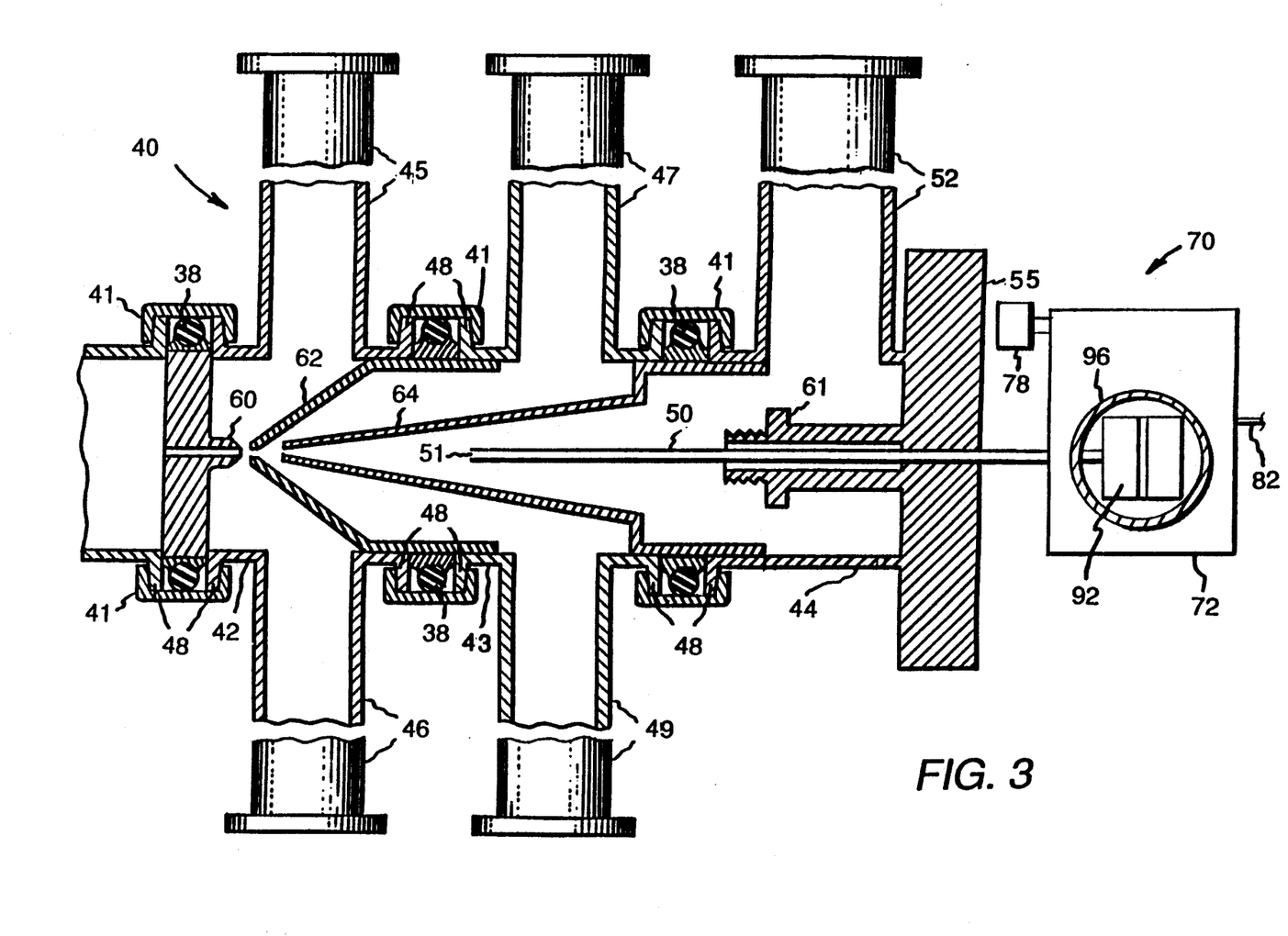
FIG. 3 is a detailed drawing of the momentum separator.

Turning to FIG. 3, evaporation chamber 22 is preferably mounted directly onto a momentum separator, generally indicated by numeral 40, by means of an end flange 41 and O-ring 38. Momentum separator 40 preferably comprises identical tubular sections 42 and 43 having flange 48 at each end, and an end section 44 having flange 48 at one end and a vacuum flange 55 at the other end. Tubular sections 42 and 43 are preferably made of stainless steel tubing and are sealably connected to each other along flanges 48. Tubular sections 42 and 43 each, are respectively provided with oppositely disposed tubes 45, 46, 47 and 49, each preferably having about 14 mm inner diameter. Tubular section 44 is preferably provided with a tube 52, having about 23 mm inner diameter. Vacuum means are connected to tubes 45, 46, 47 and 49 that serve as connecting lines to vacuum pumps, such as rotary vacuum pumps (not known) used for evacuating the various stages of momentum separator 40. The vacuum means further comprise a vacuum pump, such as a high speed and high volumetric capacity turbomolecular vacuum pump (not shown) preferably having a pumping capacity of about 190 liters/second and connected to tube 52. Preferably tube 52 has a larger diameter than tubes 45, 46, 47 and 49 for handling higher volumetric rates of gaseous components. Momentum separator 40 preferably comprises first, second and third stages, respectively formed by tubular sections 42, 43 and 44. On the first and second stage, the two pumping lines are connected to a common 20 cubic foot per minute rotary vacuum pump where each line can be isolated from the pump by means of a conventional vacuum valve, installed in each line. The first stage may be also fitted with a compression fitting, not shown, that allows the installation of an internal heater, used for heating the first stage if icing becomes a problem.

The third stage vacuum line connected to a large inner diameter tube 52 of momentum separator 40 is used to reduce pressures to a range necessary to prevent formation of a conducting path that may produce a glow discharge between the chemical ionization source and momentum separator 40. Third section 44 of momentum separator 40 comprises a stainless steel tube fitted at one end with a KF-40 flange 48 and at the other end with an "O" ring sealed vacuum flange 55 arranged to mate with a similar flange on the housing of the magnetic sector mass spectrometer. A pumping restriction between the third pumping stage and the chemical ion source of the magnetic sector mass spectrometer is provided by restricing means typically formed by a long inlet line 50. The "O" ring flange, fitted with an internal axially-positioned compression type fitting 61 serves as a mount for inlet line 50 of the restricting means, used for transporting the particle stream from momentum separator 40 to the chemical ionization chamber of the magnetic sector mass spectrometer.

Momentum separator 40 comprises three arranged to mount inside of and be firmly attached to centering rings of flanges 48. The three parts are a nozzle 60, a cone shaped first skimmer 62, and a cone shaped second skimmer 64. Nozzle 60 is preferably provided with an inside diameter of about 0.5 mm and a length of about 12.7 mm. First skimmer 62 is preferably provided with a centrally disposed opening of about 0.5 mm at the tip. In addition, the angle observed at the tip of a conic section which bisects first skimmer 62 is preferably about 67 degrees. Second skimmer 64 is preferably provided with a centrally disposed opening of about 1.0 mm at the tip. The angle observed at the tip of a conic section which bisects second skimmer 64 is preferably about 16 degrees. Nozzle 60 and the openings on first skimmer 62 and second skimmer 64 are positioned and aligned to transport the stream of particles from momentum separator 40 to the chemical ionization source of the magnetic sector mass spectrometer. Inlet line 50, preferably a glass tube, mounts in fitting 61 at the "O" ring flange end of vacuum flange 55.

Figure 4:
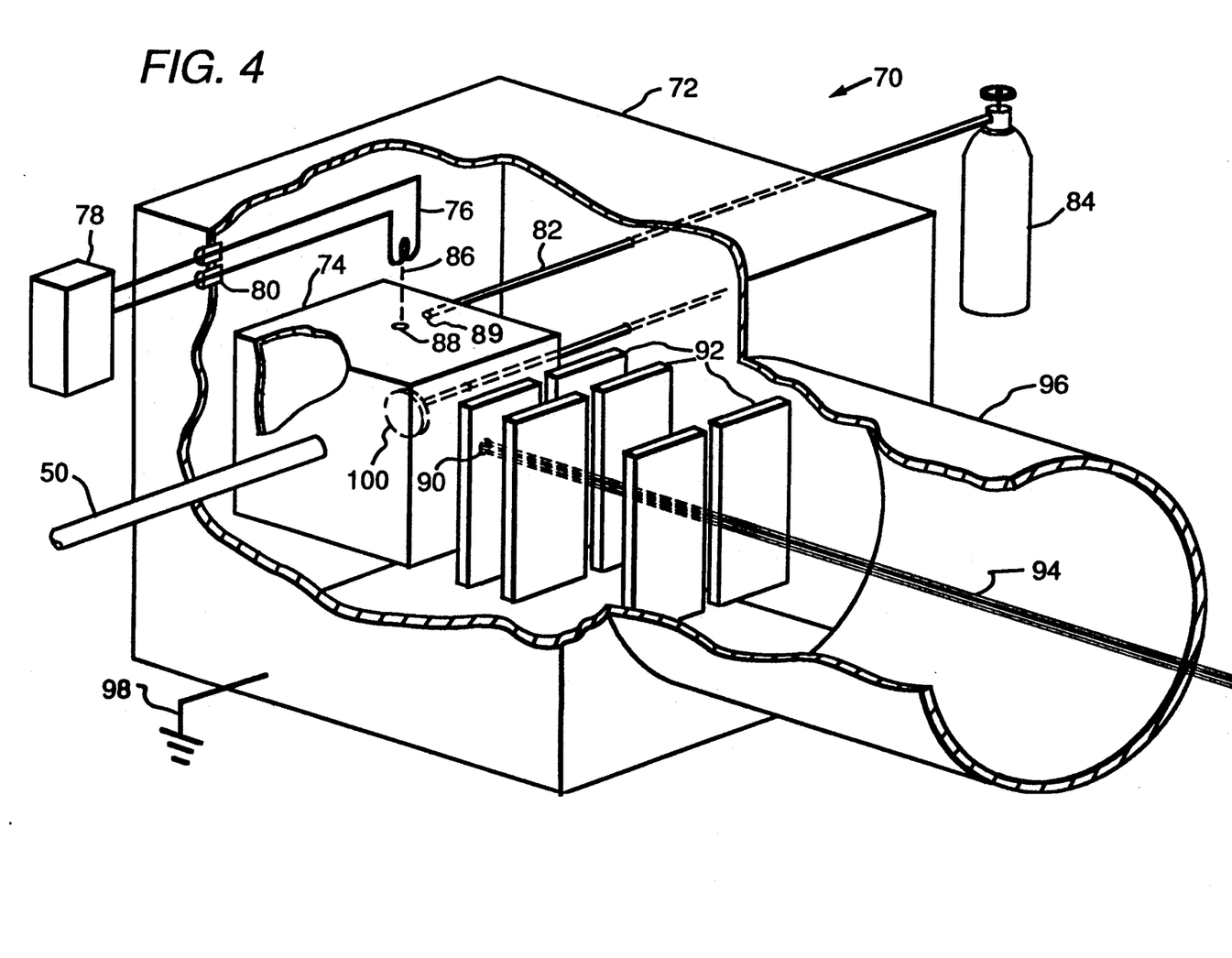
FIG. 4 is a cutaway view of a chemical ionization source.

Referring now to FIGS. 3 and 4, there is shown the chemical ionization source of the magnetic sector mass spectrometer, generally indicated by numeral 70. Chemical ionization source 70 preferably comprises a hermetically sealed housing 72 which encloses a chemical ionization block or chemical ionization chamber 74. The interior of chemical ionization housing 72 is kept under vacuum, preferably at about $5 \times 10^{-6}$ Torr, by means of a vacuum system (not shown). An entrance end 51 of inlet line 50 aligned and positioned near the opening at the tip of second skimmer 64 is connected to chamber 74 for transporting the particle stream from momentum separator 40 into chamber 74 of chemical ionization source 70. Inlet line 50 is provided with a significantly larger inner diameter, preferably about 3 mm, than inner diameter of about 0.2 mm provided in inlet lines of the conventional chemical ionization sources. Such a large diameter facilitates entry of the sample particles into chamber 74. It should be apparent to those skilled in the art to provide inlet line 50 with a demountable coupling to allow uncoupling of inlet line 50 from the chemical ionization source 70 for performing repairs or inspection. Inner diameter of inlet line 50 also acts as a restriction for isolating the final pumping stage of momentum separator 40 from the relatively high pressure (about 0.3-3.0 Torr) required by the chemical ionization process.

Chemical ionization source 70 further comprises a filament 76 used for supplying a beam 86 of electrons into chamber 74 through a window 88. Filament 76 is heated by an electrical source 78 for producing beam 86. The electrical lines used for supplying power to filament 76 are insulated from housing 72 by the insulators 80. Chamber 74 is provided with an exit orifice 90 for conveying an ion beam 94 of sample material produced in chemical ionization source 70 to the magnetic sector mass spectrometer. A reactant gas, such as a volatile hydrocarbon, may be introduced through an inlet 89 into chamber 74. Suitable hydrocarbon, such as methane or isobutane, is introduced through a pressure regulated gas line 82 connected to a reactant gas source 84. The aforementioned pressure of about 0.3 to 3.0 Torr is maintained within chamber 74 by keeping inner diameter of inlet line 50 small enough to restrict the outward flow of the reactant gas from chamber 74 and by regulating the flow rate of the reactant gas into chamber 74. Thus, a single opening provided by the inner diameter of inlet line 50 is sufficient to restrict the outward flow of the inert gas into tubular section 44 of momentum separator 40. However the single opening is large enough to transport the sample particles.

In accordance with a further aspect of the invention, chamber 74 of chemical ionization source 70 is provided with a target 100, preferably positioned in opposition to the stream of sample particles exiting from inlet line 50. Target 100 is preferably made of metal, such as copper and it is preferably heated by electrical means (not shown) for facilitating vaporization of sample particles.

Also in accordance with the invention, chemical ionization source 70 is provided with a series of plates 92 for accelerating and focussing ion beam 94 before it enters through a passage 96 into the magnetic sector mass spectrometer (not shown). Plates 92 are electrically insulated and are supplied with a variable voltage that may be regulated to provide a properly focussed ion beam 94 to the magnetic sector mass spectrometer.

Chemical ionization housing 72 is grounded through a ground 98 and chamber 74 is connected to a high voltage source (not shown) capable of providing voltages in the range of about 8–10 KeV. Since inlet line 50 is connected to chamber 74, it is also subjected to high voltages. If entrance end 51 of inlet line 50 is too close to a component of momentum separator 40, such as the inner wall of skimmer 64, an electrical glow discharge may occur between the two. Such a discharge is very damaging to the equipment. The aforementioned problem is solved in the present invention by sufficiently separating the inner wall of skimmer 64 and entrance end 51 of inlet line 50 to prevent the electrical glow discharge.

It should be apparent to those skilled in the art to combine chemical ionization source 70 of the present invention with a conventional electron impact ionization source, if required.

When all of the mechanical components are connected using KF type flanges, each of the parts can be readily demounted for adjustment or modification. The positions of each of the skimmers, the nozzle and the glass inlet line are all adjustable horizontally along the axis of the momentum separator by axially sliding skimmers 62 and 64 on the inner diameter of tubular section 43 and 44. The preferred positions of the various components are as follows:

1) Tip of first skimmer 62 about 3 mm behind the tip of the nozzle 60;

2) Tip of second skimmer 64 about 5 mm behind the nearest point of contact on the inside wall of first skimmer 62; and 3) Entrance end 51 of inlet line 50 about 15 mm behind the nearest point of contact on the inside wall of second skimmer 64 for preventing an electrical glow discharge.

Minor adjustments in the axial alignments of the nozzle and the various skimmers are possible because of slight side play where the centering rings make contact with the flanges. Using this adjustment, the alignments have been optimized optically to ensure that the orifices are strictly concentric with each other.

When operating, nebulizer 10 is supplied with the effluent output of the liquid chromatograph and with a flow of helium amounting to about 1000 ml/min. With an applied power of about 3.8 watts, ultrasonic nebulizer 10 produces an aerosol with particle sizes ranging from about 10–50 microns. These particles are dispersed by the helium jet and travel into evaporation chamber 20. In evaporation chamber 20, the eluent from these aerosol particles is evaporated. This process of evaporation causes cooling of the droplet which, if not compensated, can cease evaporation. Such a cooling is compensated by providing a heated carrier gas, e.g., helium. The helium itself is heated by coiled heater 27 described above. Sufficient heat input is ensured by monitoring the temperature of the gas at the end of evaporation chamber 20. A significant number of aerosol particles does not impact on heater 27 because as a particle approaches heater 27 it tends to lose solvent more quickly on the heated side thereby generating an asymmetrical force on the particle with a net vector sum directed away from the hot surface. Under most conditions, the vacuum in evaporation chamber 20 is about 508 Torr. Care must be taken not to allow the pressure to become too low because this may inhibit drying of the particles by reducing the contact time between the particles and the helium.

In passing through evaporation chamber 20, the aerosol is evaporated and it arrives at the entrance to nozzle 60 as a mixture of helium, solvent vapor, and small dry particles of the sample. The strong pumping pressure provided by the vacuum pumps connected to momentum separator 40 generates a high velocity flow through nozzle 60 by providing momentum to the sample particles. This accelerates the sample particles to sonic velocities. Because the sample particles are much more massive than the associated inert gas, usually helium gas, and solvent vapor, these particles have much greater momentum and tend to travel in a straight line after leaving nozzle 60. On the other hand, the gaseous components exiting from the nozzle jet tend to be pumped away by the action of the rotary vacuum pumps connected to momentum separator 40 and also due to the cone shapes of skimmers 62 and 64 respectively. Most of the gas (about 97%) is removed in the first stage of momentum separator 40. The later stages serve to remove the last traces of solvent vapor and helium gas, leaving the sample particles to continue their trip to chemical ionization source 70 effectively free of solvent vapor. Due to large inner diameter of inlet line 50, the reactant gas from chamber 74 tends to exit out of inlet line 50 into third section 44 of momentum separator 40. Such an escaped reactant gas should be evacuated rapidly to prevent formation of conducting paths that create electrical glow discharge between entrance end 51 of inlet line 50 and the inner side of skimmer 64. By connecting to tube 52 of the third section of momentum separator 40 the high volumetric rate turbomolecular vacuum pump and by maintaining vacuum therein of about $3 \times 10^{-2}$ Torr, possibility of the electrical glow discharge is significantly reduced. Additionally, by allowing the outward flow of the reactant gas into third section 44 of momentum separator 40 and not in the interior of chemical ionization chamber 74, the vacuum system of the magnetic sector mass spectrometer is not burdened.

Chemical ionization mass spectra result from the ionmolecule reactions that occur between the sample particles at low pressure and the primary ions of a high pressure reactant gas. Typical pressures in chemical ionization chamber 74 vary between about 0.3–3.0 Torr for the reactant gas. Both gas upon introduction into chemical ionization chamber 74, are bombarded by electron beam 86. Since the amount of the sample material in chemical ionization chamber 74 is significantly less than the amount of the reactant gas, virtually all of the primary ionization by electron beam 86 occurs to the reactant gas. The ionized reactant gas undergoes ion-molecule reactions with itself to form a steady-state plasma which in turn reacts chemically with the sample particles. The process results in ionizing the sample particles. If methane is used as the reactant gas, the most important ions in the reaction plasma are $CH_5^+$ and $C_2H_5^+$ which together make up to about 90% of the ionic content. It is believed, even though no reliance thereon is intended, that these ions are formed by a reaction of the normal electron impact products with the excess of $CH_4$ in the chemical ionization chamber 74. Thus:

$$CH_4 + e \rightarrow CH_4^+ + 2e$$

$$CH_4 \rightarrow CH_3^+ + H.$$

$$CH_4^+ + CH_4 \rightarrow CH_5^+ + CH_3$$

$$CH_3^+ + CH_4 \rightarrow C_2H_5^+ + H_2$$

In the presence of a good proton acceptor, such as dipropyl phthalate (1,2-benzenedicarboxylic acid dipropyl ester, $C_{14}H_{18}O_4$), the ions $CH_5^+$ and $C_2H_5^+$ act as Bronsted acids and protonate the molecule:

$$CH_5^+ + C_{14}H_{18}O_4 \rightarrow [C_{14}H_{18}O_4] + H + CH_4$$

$$C_2H_5^+ + C_{14}H_{18}O_4 \rightarrow [C_{14}H_{18}O_4] + H + C_2H_4$$

These reactions are typical of those observed for alcohols, aldehydes, esters, etc., and also for many biochemical compounds, typically encountered in recent chemical ionization applications.

Additional fragmentation occurs in chamber 74 to give a mass spectral pattern that is similar in appearance to the electron impact spectrum of a hydrocarbon, but the abundance of the quasi-parent ion is greatly increased relative to the fragment ions.

The increased relative abundance of the quasi-parent ion has proven to be of great value in many studies, particularly with relatively complex bioorganic molecules. As studies of the fragmentation patterns are extended and the various effects of different reactant gases are understood and applied, chemical ionization spectra have proven to have increased value. One of the important reasons that this increased quasi-parent ion abundance is so useful is that the overall mass spectral sensitivity is of the same order of magnitude as the sensitivity obtained for electron impact spectra. High sensitivity occurs due in part, to the fact that the electron beam is fully utilized because of the considerable increase in the partial pressure of reactant gas in chamber 74. The reactant gas or ion plasma, in turn, has a high probability of reactive collision with the unknown sample; thus the overall sensitivity is quite comparable to that obtained by conventional electron impact ionization source.

The present invention will be further understood from the illustration of specific examples which follow. These examples are intended for illustrative purposes only and should not be construed as limitation upon the broadest aspects of the invention.

EXAMPLES

Figure 5:
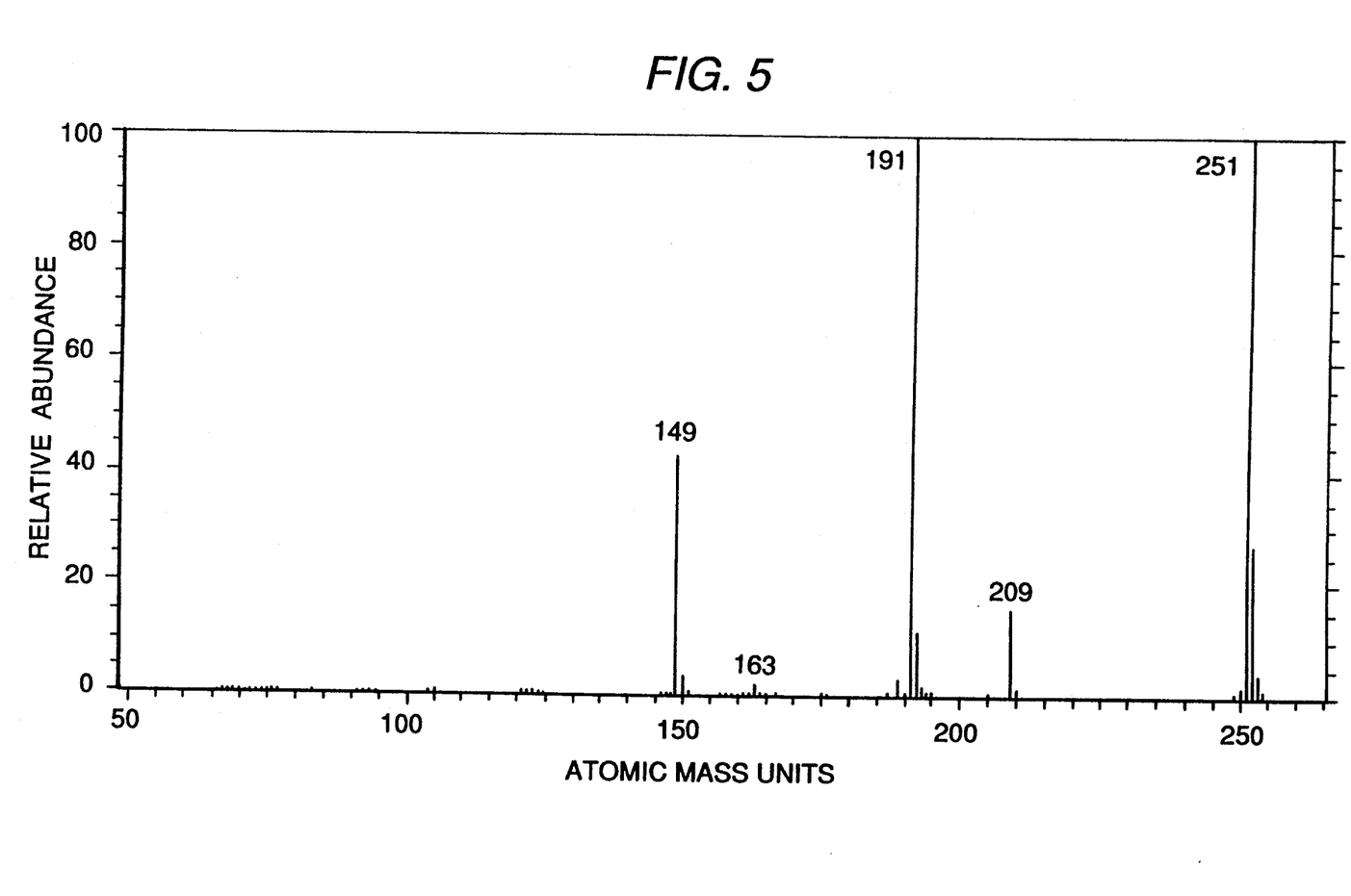
FIG. 5 is a mass spectrum of dipropyl phthalate obtained by using chemical ionization source of the present invention.

Relative abundance of dipropyl phthalate having a molecular weight of 250 was analyzed by using the improved interface of the present invention having the chemical ionization source therein. FIG. 5 shows the mass spectrum of dipropyl phthalate. As seen in FIG. 5, the molecular fragmentation of dipropyl phthalate is significantly minimized and spectral lines indicating its presence is clearly shown.

Figure 6:
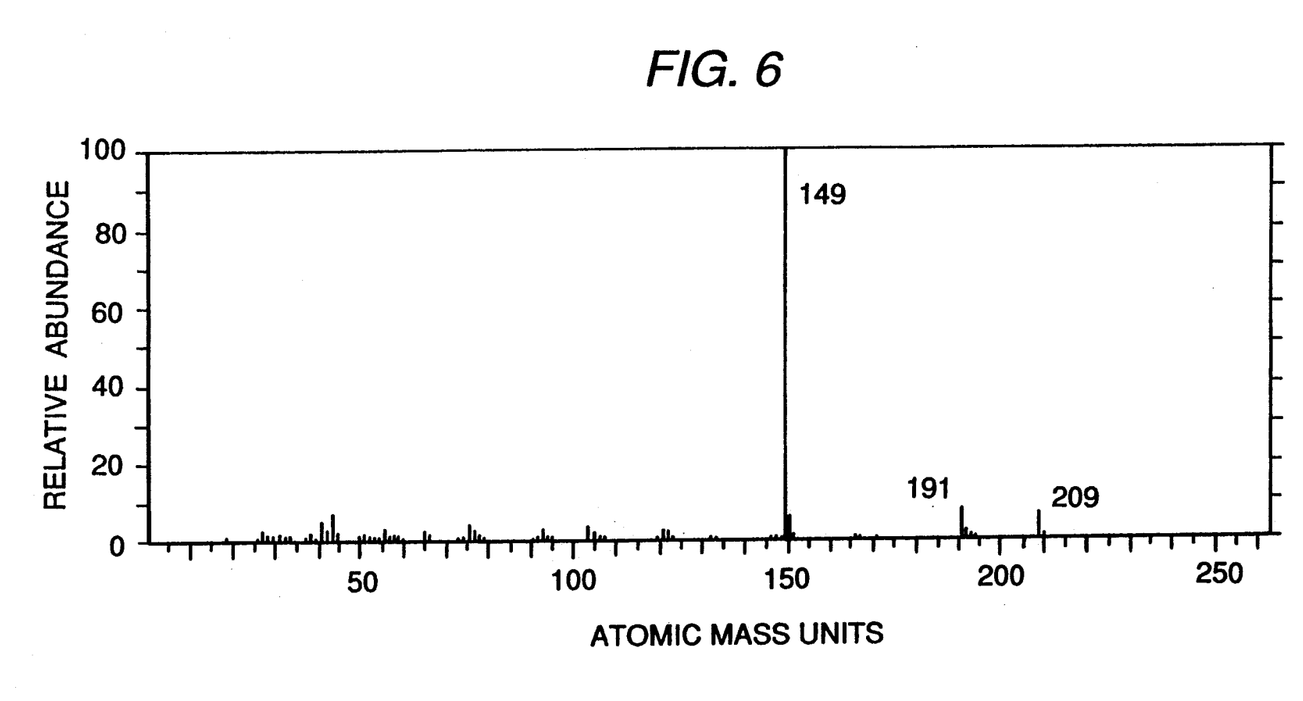
FIG. 6 is a mass spectrum of dipropyl phthalate obtained by using conventional electron impact ionization source.

FIG. 6 shows the mass spectrum of dipropyl phthalate obtained by using conventional electron impact ionization source. FIG. 6 shows significant molecular fragmentation of dipropyl phthalate and as a result hardly any spectral lines are present at 250 which would have indicated presence of dipropyl phthalate.

What is claimed is:

1. An apparatus for interfacing a liquid chromatograph with a magnetic sector mass spectrometer having a chemical ionization source therein, said apparatus comprising:

nebulizing means for providing both ultrasonic and pneumatic nebulization under partial vacuum to a chromatograph effluent and dispersing the resultant particles by a flow of inert gas to produce an aerosol stream of said particles;

evaporation means for evaporating liquid chromatograph solvent into gaseous components from said stream, said evaporation means having heater means therein for maintaining, through feedback temperature control means, the temperature of said aerosol stream of particles and for compensating the cooling of said stream of said effluent due to evaporation of said liquid chromatograph solvent;

a momentum separator connected to said evaporation means, said momentum separator having three stages and means for providing momentum to said particles in said stream and further having vacuum means at each of said stages for removing the gaseous components present in said stream; and restricting means connected to said momentum separator and to a chemical ionization block of said chemical ionization source, said restricting means having a single opening small enough to restrict the outward flow of a reactant gas from said block to said momentum separator but large enough to transport said sample particles from said momentum separator to said chemical ionization block of said chemical ionization source.

2. The apparatus according to claim 1 wherein said first and said second stage further comprises cone shaped skimmers having openings that allow passage said sample particles from said evaporation means to said restricting means.

3. The apparatus according to claim 2 wherein said skimmers of said first and second stage of said momentum separator are symmetrically pumped by said vacuum means from two directions.

4. The apparatus according to claim 1 wherein said restricting means further comprise an entrance end proximately positioned near said third stage of said momentum separator and an exit end connected to said chemical ionization block, said entrance end of said restricting means being sufficiently separated from said third stage and said vacuum means having sufficient pumping capacity to prevent an electrical glow discharge between said transporting means and said third stage.

5. The apparatus according to claim 4 wherein said entrance end of said restricting means is aligned with and positioned near said opening of said skimmer of said second stage of said momentum separator.

6. The apparatus according to claim 1 wherein said vacuum means in said first and second stages of said momentum separator are rotary vacuum pumps and in said third stage a turbomolecular vacuum pump having a pumping capacity of about 190 liters per second.

7. The apparatus according to claim 1 wherein said restricting means is a glass tube having an inner diameter of about 3 millimeters.

8. The apparatus according to claim 1 wherein said opening is about 3 millimeters.

9. An apparatus for interfacing a liquid chromatograph with a magnetic sector mass spectrometer having a chemical ionization source therein, said apparatus comprising:

nebulizing means for providing both ultrasonic and pneumatic nebulization under partial vacuum to a chromatograph effluent and dispersing the resultant particles by a flow of inert gas to produce an aerosol stream of said particles;

evaporation means for evaporating liquid chromatograph solvent into gaseous components from said stream, said evaporation means having heater means therein for maintaining, through feedback temperature control means, the temperature of said aerosol stream of particles and for compensating the cooling of said stream of said effluent due to evaporation of said liquid chromatograph solvent;

a momentum separator connected to said evaporation means, said momentum separator having three stages and means for providing momentum to said particles in said stream and further having vacuum means at each of said stages for removing the gaseous components present in said stream; and restricting means having an entrance end proximately positioned near said third stage of said momentum separator and an exit end connected to a chemical ionization block of said chemical ionization source, said restricting means having a single opening small enough to restrict the outward flow of a reactant gas from said block to said momentum separator but large enough to transport said sample particles from said momentum separator to said chemical ionization block of said chemical ionization source, said entrance end of said restricting means being sufficiently separated from said third stage and said vacuum means having sufficient pumping capacity to prevent an electrical glow discharge between said restricting means and said third stage of said momentum separator.

* * * * *